US011517395B2

(12) United States Patent
Matsuura et al.

(10) Patent No.: US 11,517,395 B2
(45) Date of Patent: Dec. 6, 2022

(54) CONTROL DEVICE, CONTROL METHOD, AND SURGICAL SYSTEM

(71) Applicant: SONY CORPORATION, Tokyo (JP)

(72) Inventors: Kana Matsuura, Kanagawa (JP); Takeshi Maeda, Tokyo (JP); Seiji Wada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 397 days.

(21) Appl. No.: 16/614,440

(22) PCT Filed: May 11, 2018

(86) PCT No.: PCT/JP2018/018253
§ 371 (c)(1),
(2) Date: Nov. 18, 2019

(87) PCT Pub. No.: WO2018/216501
PCT Pub. Date: Nov. 29, 2018

(65) Prior Publication Data
US 2020/0179077 A1 Jun. 11, 2020

(30) Foreign Application Priority Data
May 26, 2017 (JP) .............................. JP2017-104131

(51) Int. Cl.
*A61B 90/00* (2016.01)
*A61B 90/25* (2016.01)
(Continued)

(52) U.S. Cl.
CPC ........ *A61B 90/361* (2016.02); *A61B 1/00188* (2013.01); *A61B 1/045* (2013.01); *A61B 90/25* (2016.02); *A61B 90/50* (2016.02)

(58) Field of Classification Search
CPC ... A61B 90/361; A61B 1/00188; A61B 1/045; A61B 90/25; A61B 90/50;
(Continued)

(56) References Cited

U.S. PATENT DOCUMENTS

2010/0185212 A1* 7/2010 Sholev .................. A61B 90/50
600/102
2013/0169412 A1* 7/2013 Roth ...................... H01H 21/26
340/6.1
(Continued)

FOREIGN PATENT DOCUMENTS

JP    08-299364 A    11/1996
JP    2012-223363 A  11/2012
(Continued)

OTHER PUBLICATIONS

International Search Report and Written Opinion of PCT Application No. PCT/JP2018/018253, dated Aug. 14, 2018, 07 pages of ISRWO.

*Primary Examiner* — Tracy Y. Li
(74) *Attorney, Agent, or Firm* — Chip Law Group

(57) ABSTRACT

The present technology relates to a control device, a control method, and a surgical system that enable an operator to implement operation without a burden. A control unit controls a plurality of patterns of operations of a surgical instrument, and an acquisition unit obtains motion information indicating a motion of a user. Furthermore, the control unit controls the operations of the respective patterns corresponding to the motion information obtained by the acquisition unit in parallel using only a single operation performed by the user as a trigger. The present technology can be applied to a control device of a surgical system.

8 Claims, 9 Drawing Sheets

(51) Int. Cl.
*A61B 1/00* (2006.01)
*A61B 1/045* (2006.01)
*A61B 90/50* (2016.01)

(58) Field of Classification Search
CPC .......... A61B 2017/00203; A61B 2017/00207; A61B 2017/00216; A61B 2017/00973; A61B 2034/2065; A61B 2090/368; A61B 2090/371; G06F 3/01; G06F 3/0346
See application file for complete search history.

(56) References Cited

U.S. PATENT DOCUMENTS

| | | | | |
|---|---|---|---|---|
| 2016/0147410 A1* | 5/2016 | Nam | ....................... | G06F 3/005 345/158 |
| 2017/0068081 A1 | 3/2017 | Hirayama | | |
| 2018/0173306 A1* | 6/2018 | Okabe | ..................... | G10L 15/22 |

FOREIGN PATENT DOCUMENTS

| | | | |
|---|---|---|---|
| JP | 2015-192697 A | 11/2015 | |
| WO | 2015/151447 A1 | 10/2015 | |
| WO | 2017/061294 A1 | 4/2017 | |

* cited by examiner

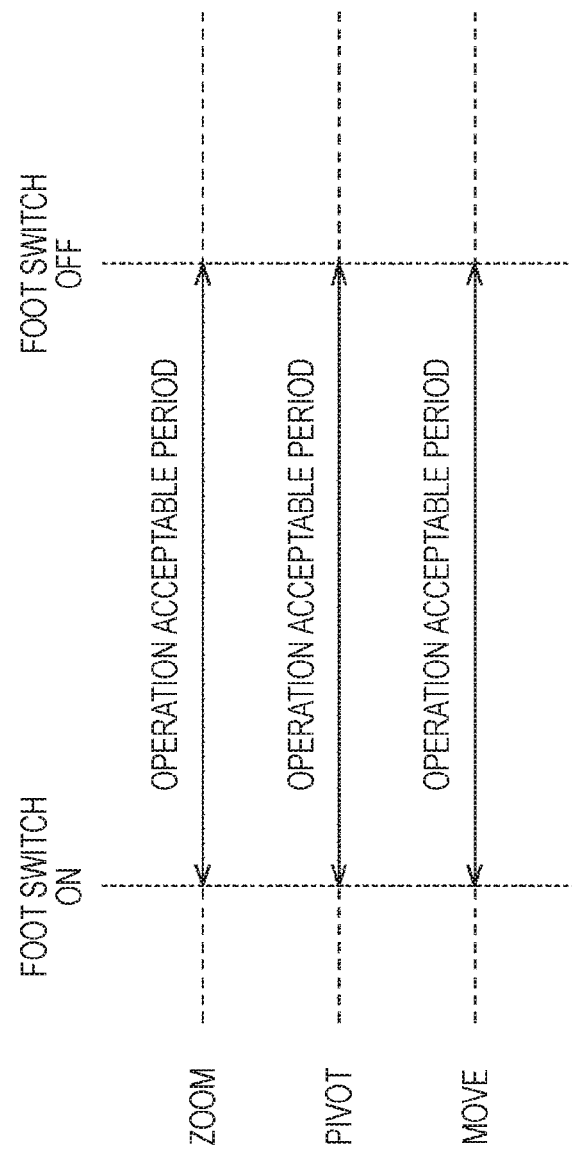

CONTROL DEVICE, CONTROL METHOD, AND SURGICAL SYSTEM

CROSS REFERENCE TO RELATED APPLICATIONS

This application is a U.S. National Phase of International Patent Application No. PCT/JP2018/018253 filed on May 11, 2018, which claims priority benefit of Japanese Patent Application No. JP 2017-104131 filed in the Japan Patent Office on May 26, 2017. Each of the above-referenced applications is hereby incorporated herein by reference in its entirety.

TECHNICAL FIELD

The present technology relates to a control device, a control method, and a surgical system, and more particularly, to a control device, a control method, and a surgical system that enable an operator to implement operation without a burden.

BACKGROUND ART

Conventionally, there is a surgical system in which operation of each of a camera and a camera arm is associated with an individual trigger. For example, zoom control of a camera and drive control of a camera arm are carried out using a foot switch unit in which multiple switches are combined.

Furthermore, there has also been known a technique of causing a camera to follow a line of sight position of an operator in the surgical system. For example, Patent Document 1 discloses that an imaging angle of a camera is changed without changing a distance between the camera and a gaze point of a user on the basis of movement of the user and the gaze point.

In such a surgical system, operation of each of the camera and the camera arm is specified by a motion or movement of the operator.

CITATION LIST

Patent Document

Patent Document 1: Japanese Patent Application Laid-Open No. 2015-192697

SUMMARY OF THE INVENTION

Problems to be Solved by the Invention

However, it is not appropriate to force the operator to perform further operations in the state where hands are occupied due to high-level and delicate operations, such as surgical procedures.

The present technology has been conceived in view of such a situation, and it is an object to enable an operator to implement operation without a burden.

Solutions to Problems

A control device according to the present technology includes a control unit that controls a plurality of patterns of operations of a surgical instrument, and an acquisition unit that obtains motion information indicating a motion of a user, in which the control unit controls the operations of the respective patterns corresponding to the motion information obtained by the acquisition unit in parallel using only a single operation performed by the user as a trigger.

A control method according to the present technology, which is performed by a control device that controls a plurality of patterns of operations of a surgical instrument, includes steps of obtaining motion information indicating a motion of a user, and controlling the operations of the respective patterns corresponding to the obtained motion information in parallel using only a single operation performed by the user as a trigger.

A surgical system according to the present technology includes a surgical instrument and a control device that controls the surgical instrument, in which the control device includes a control unit that controls a plurality of patterns of operations of the surgical instrument, and an acquisition unit that obtains motion information indicating a motion of a user, and the control unit controls the operations of the respective patterns corresponding to the motion information obtained by the acquisition unit in parallel using only a single operation performed by the user as a trigger.

In the present technology, a plurality of patterns of operations of a surgical instrument is controlled, motion information indicating a motion of a user is obtained, and the operations of the respective patterns corresponding to the obtained motion information are controlled in parallel using only a single operation performed by the user as a trigger.

Effects of the Invention

According to the present technology, it becomes possible to enable an operator to implement operation without a burden.

Note that the effects described herein are not necessarily limited, and may be any of the effects described in the present disclosure.

BRIEF DESCRIPTION OF DRAWINGS

FIG. 5 is a diagram illustrating an operation acceptable period.

MODE FOR CARRYING OUT THE INVENTION

Hereinafter, a mode for carrying out the present disclosure (hereinafter referred to as an embodiment) will be described. Note that descriptions will be given in the following order.

1. Exemplary Configuration of Conventional Foot Switch Unit for Surgery
2. Overview of Surgical System
3. Operation Control of Operative Field Camera and Camera Arm
4. Exemplary Functional Configuration of Control Device
5. Control Process Flow in Surgical System
6. Variation <1. Exemplary Configuration of Conventional Foot Switch Unit for Surgery>

Figure 1:
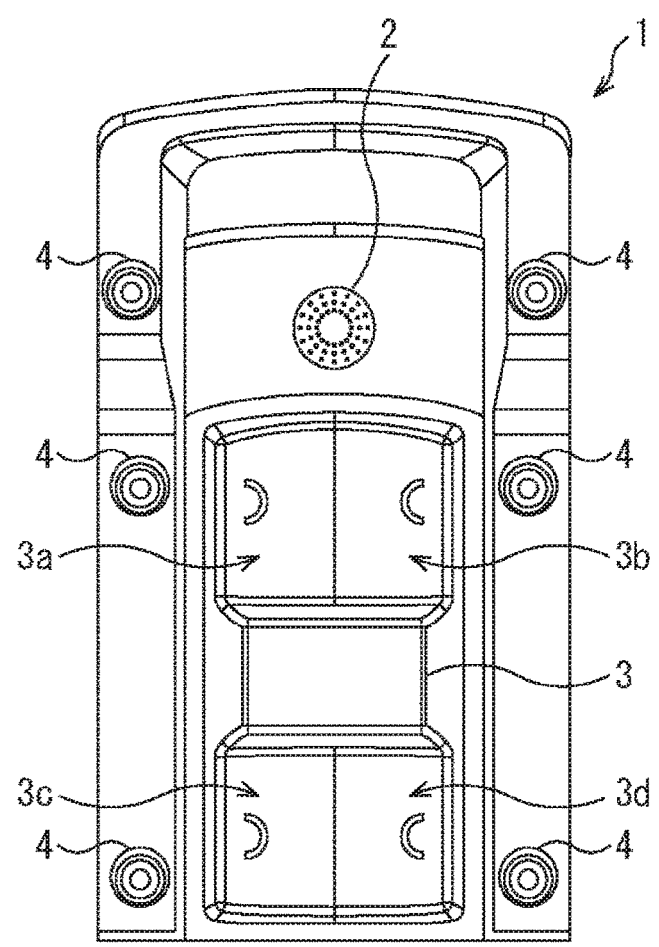
FIG. 1 is a top view illustrating an exemplary configuration of an appearance of a conventional foot switch unit for surgery.

FIG. 1 is a top view illustrating an exemplary configuration of an appearance of a conventional foot switch unit for surgery.

A foot switch unit 1 in FIG. 1 includes a lever 2, a step-in section 3, and six push buttons 4.

The lever 2 is configured as what is called a joystick, and receives operation input made by an operator's foot. With the lever 2 being operated in the cross direction, for example, a camera is positioned.

The step-in section 3 is configured as a physical button as a whole, and receives operation input made by the operator's foot. With an upper left portion 32a, an upper right portion 32b, a lower left portion 32c, and a lower right portion 32d of the step-in section 3 being stepped, for example, zoom control or focus control of the camera is performed according to the stepped portion.

Each of the push buttons 4 is configured as a physical button, and receives operation input made by the operator's foot. With the push button 4 being pressed, for example, a function programmed beforehand or the like is executed.

The foot switch unit 1 is configured to be larger than the size of the operator's foot as a whole, and the operator operates the lever 2, the step-in section 3, and the push buttons 4 by fully utilizing his/her entire foot or fingers.

Incidentally, in a surgical system, it is not appropriate to force the operator to perform further operations in the state where hands are occupied due to high-level and delicate operations, such as surgical procedures. In addition, complex operation tends to cause an operation error, and the error may lead to an unexpected accident.

In particular, in a system using a plurality of types of operation units, such as the foot switch unit 1 in FIG. 1, visual confirmation is required to avoid operation errors, which is inefficient. While some operators take off their shoes to perform operation to catch a shape of the foot switch unit with the feeling of their soles, essentially, taking off their shoes in an operating room is dangerous and should be avoided.

Moreover, in a system that requires frequent switch operations, such as mode switching, it takes an extra time as the operator's motions for the operation increases, for example. It is not preferable that the operation takes an extra time in surgery involving a long operation.

In view of the above, in the surgical system to which the present technology is applied, a camera and a camera arm are controlled in response to a natural motion of the operator using only a single operation as a trigger, thereby implementing operation without a burden on the operator.

<2. Overview of Surgical System>

Figure 2:
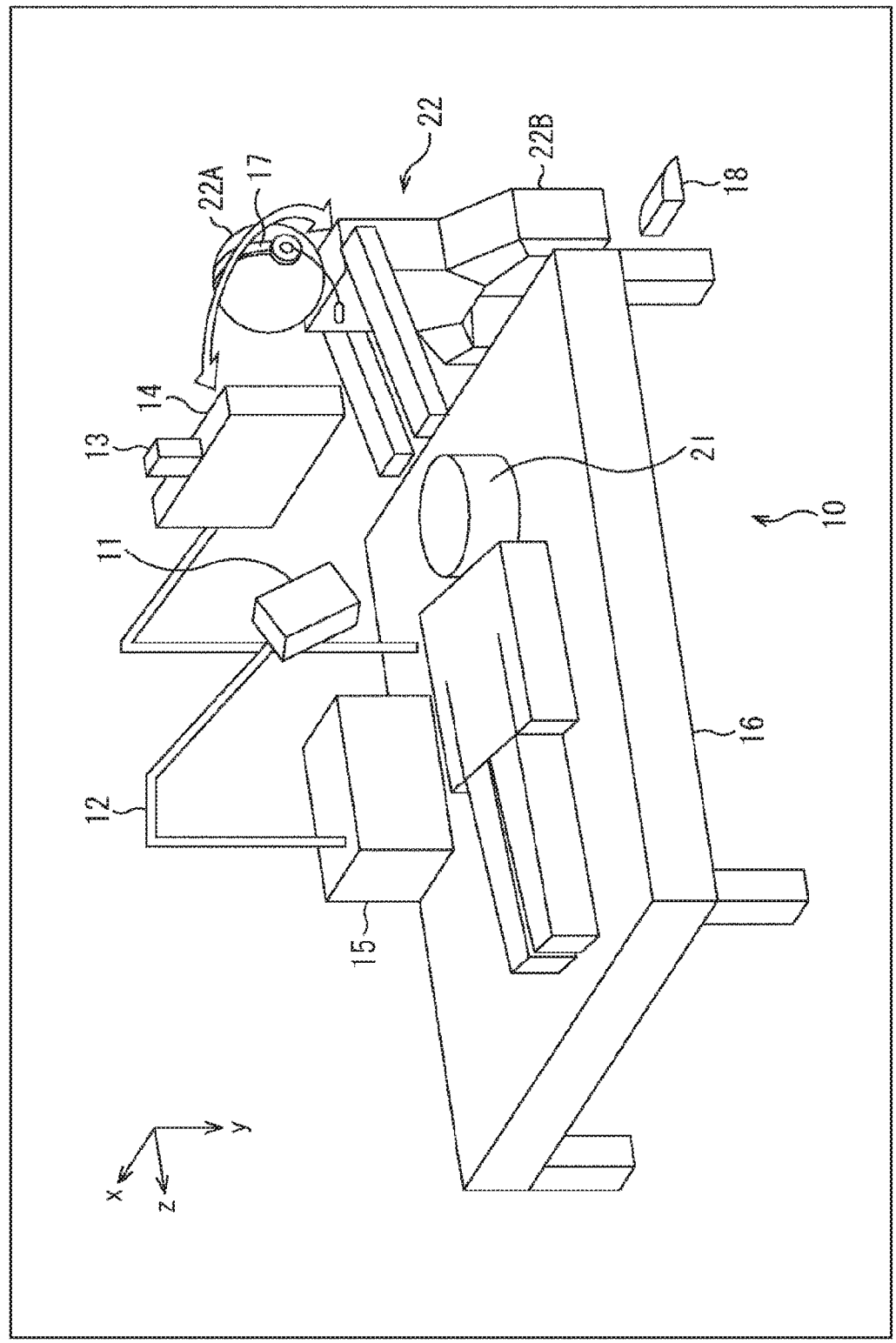
FIG. 2 is a diagram illustrating an exemplary configuration of a surgical system to which the present technology is applied.

FIG. 2 is a block diagram illustrating an exemplary configuration of the surgical system to which the present technology is applied.

A surgical system 10 includes an operative field camera 11, a camera arm 12, a motion recognition camera 13, a display 14, a control device 15, a surgical table 16, a microphone 17, and a foot switch 18. The surgical system 10 is installed in an operating room or the like, and enables a procedure such as surgery with reference to an image captured by the operative field camera 11.

The operative field camera 11 is a modality device, such as a 3D camera supported by the camera arm 12. The operative field camera 11 captures an image of, for example, the operative field of a patient 21 lying on the surgical table 16, and transmits, to the control device 15, a 3D image obtained as a result of the imaging as an operative field image. The camera arm 12 supports the operative field camera 11, and controls the position and the angle of the operative field camera 11.

The motion recognition camera 13 is, for example, a 2D camera, and is disposed on the display 14. The motion recognition camera 13 captures an image of an operator 22 (user) wearing the microphone 17 on his/her head 22A. The motion recognition camera 13 transmits, to the control device 15, a 2D image obtained as a result of the imaging as an operator image.

The display 14 is a 3D display having a relatively small screen, and is disposed at a position relatively close to the operator 22 (position on the surgical table 16 close to the operator 22 in the example of FIG. 2). The display 14 displays the operative field image and the like transmitted from the control device 15.

The control device 15 sets the control mode of the surgical system 10 to a manual mode or a hands-free mode. The manual mode is a mode in which the surgical system 10 is controlled on the basis of manual input made by the operator 22 (e.g., force application to the camera arm 12, and operation of operation buttons (not illustrated) or the like provided in respective parts). The hands-free mode is a mode in which the surgical system 10 is controlled on the basis of non-contact input, such as a voice, a line of sight, a motion and a direction of the head 22A, and gesture not manually made by the operator 22, or input made by contact of a leg 22B to the foot switch 18.

Hereinafter, operation in the case where the control mode is the hands-free mode will be mainly described.

The control device 15 detects the position of the head 22A in the operator image transmitted from the motion recognition camera 13, thereby recognizing the motion and the direction of the head 22A. Furthermore, the control device 15 detects the direction of the line of sight of the operator 22 from the operator image, and recognizes, on the basis of the direction, the position of the line of sight on the screen of the display 14.

Note that, although the detection of the line of sight is carried out using the operator image captured by the motion recognition camera 13 in the surgical system 10, the operator 22 may wear glasses equipped with a line-of-sight detecting device so that the line-of-sight detecting device detects a line of sight.

Furthermore, although the motion and the direction of the head 22A is detected from the operator image as the distance between the motion recognition camera 13 and the operator 22 is short in the surgical system 10, the operator 22 may wear a marker and the motion and the direction of the head 22A may be detected from the position of the marker in the operator image.

The control device 15 receives a voice transmitted from the microphone 17, and performs voice recognition on the voice. The control device 15 receives operation signals indicating operation made on the foot switch 18, which are transmitted from the foot switch 18, and recognizes the content of the operation made on the foot switch 18 on the basis of the operation signals.

In particular, in a case where the control mode is the hands-free mode, the control device 15 sets, as input information, motion information indicating motions of the operator 22, such as a motion and a direction of the head 22A, gesture of the operator 22, line-of-sight position information indicating a position of a line of sight on the screen of the display 14, a voice recognition result, and a sound volume, and operation information indicating operation made on the foot switch 18. The control device 15 recognizes a command from the operator 22 on the basis of the input information.

The control device 15 controls imaging performed by the operative field camera 11, controls driving of the camera arm 12, controls a display of the display 14, or changes the control mode in response to the command from the operator 22.

The microphone 17 is attached to the head 22A of the operator 22. The microphone 17 obtains a surrounding voice including a voice of the operator 22 and the like, and transmits the voice to the control device 15.

The foot switch 18 is an input unit disposed around the operator 22, and is operated by contact of the leg 22B of the operator 22.

Furthermore, the foot switch 18 receives only a single operation made by the leg 22B of the operator 22. For example, while the foot switch 18 may have a plurality of buttons, a pedal, and the like, only stepping on the pedal is accepted in a case where the control mode is the hands-free mode. The single operation performed on the foot switch 18 is not limited to stepping on the pedal, and may be pressing of any of the plurality of buttons. The foot switch 18 transmits, to the control device 15, operation signals indicating operation made by the leg 22B of the operator 22.

In the surgical system 10 configured as described above, the operator 22 lays the patient 21 on the surgical table 16, and performs surgery or the like while viewing the operative field image or the like displayed on the display 14.

Furthermore, the operator 22 makes non-contact input or input based on foot contact in the case of changing an imaging condition of the operative field camera 11, a position or an angle of the operative field camera 11, a display of the display 14, or the like. Therefore, the operator 22 can make input while holding a surgical instrument (not illustrated), and does not need to perform sterilization processing each time the input is made.

Note that any method can be adopted as a method of detecting a line of sight, a method of detecting a motion and a direction of the head 22A of the operator 22, a method of detecting gesture, and a method of obtaining voice. For example, the line-of-sight detecting device or the microphone 17 may not be a wearable device.

Furthermore, hereinafter, the horizontal direction of the display 14 will be referred to as an x direction, the vertical direction will be referred to as a y direction, and a direction perpendicular to the screen of the display 14 will be referred to as a z direction.

<3. Operation Control of Operative Field Camera and Camera Arm>

Next, operation control of the operative field camera 11 and the camera arm 12 in the surgical system 10 will be described.

(Operation Pattern of Operative Field Camera and Camera Arm)

Figure 3C:
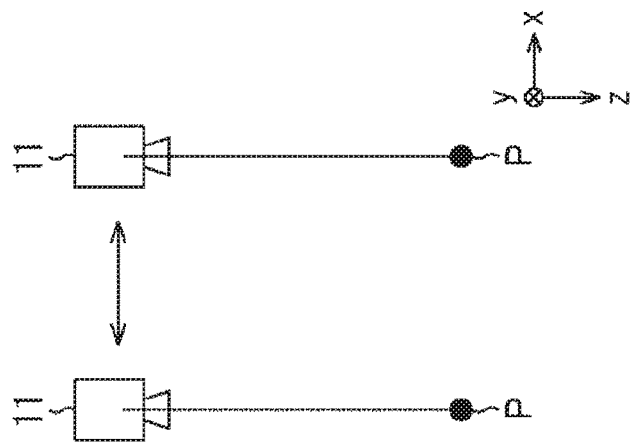
FIGS. 3A, 3B, and 3C are diagrams illustrating an operation pattern of an operative field camera and a camera arm.
Figure 3B:
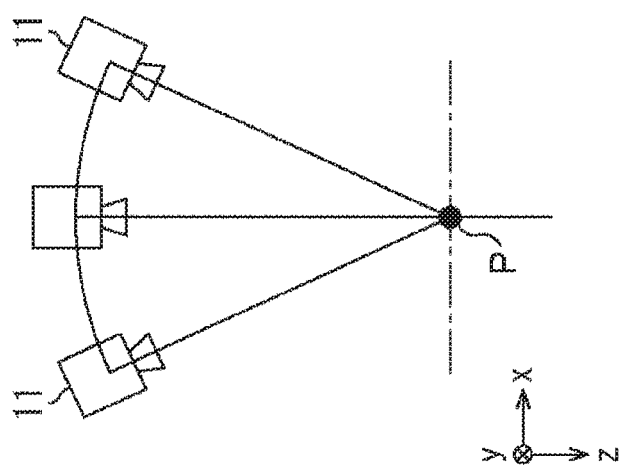
Figure 3A:

FIGS. 3A, 3B, and 3C are diagrams illustrating an operation pattern of the operative field camera 11 and the camera arm 12 in FIG. 1.

First, as illustrated in FIG. 3A, the operative field camera 11 can perform zoom operation without changing its position. Specifically, the operative field camera 11 can scale the center P of the operative field to be imaged by performing zoom control. In the zoom control of the operative field camera 11, optical zoom control may be performed, or digital zoom control may be performed.

Next, as illustrated in FIG. 3B, the operative field camera 11 can perform pivot operation of changing an imaging angle without changing the imaging center. Specifically, the operative field camera 11 can move on the basis of the drive control of the camera arm 12 such that the distance from the center P of the operative field to be imaged is constant at all times. Accordingly, the operative field camera 11 can capture operative field images having the same center P of the operative field and different imaging angles.

Besides, as illustrated in FIG. 3C, the operative field camera 11 can perform move operation in the x direction for moving the imaging center in the x direction. Specifically, the operative field camera 11 can move in the x direction on the basis of the drive control of the camera arm 12. Accordingly, the operative field camera 11 can move the center P of the operative field to be imaged in the x direction.

Moreover, although illustration is omitted, the operative field camera 11 can also perform the move operation in the y direction or in the z direction on the basis of the drive control of the camera arm 12. In a case where the operative field camera 11 performs the move operation in the y direction, the operative field camera 11 can move the center P of the operative field to be imaged in the y direction. Furthermore, in a case where the operative field camera 11 performs the move operation in the z direction, the operative field camera 11 can scale the imaging range.

Note that, although the move operation of the operative field camera 11 is performed by the camera arm 12 moving the operative field camera 11 in the present embodiment, it may be performed by the camera arm 12 changing the imaging angle of the operative field camera 11.

(Method of Operating Operative Field Camera and Camera Arm)

Next, an operation method for controlling operation of each pattern of the above-described operative field camera 11 and the camera arm 12 will be described with reference to FIGS. 4A, 4B, and 4C.

Figure 4C:
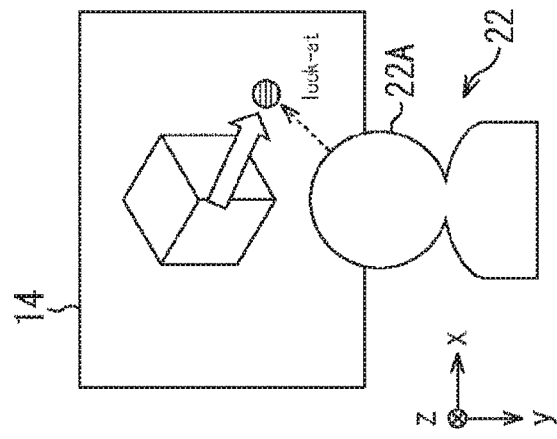
FIGS. 4A, 4B, and 4C are diagrams illustrating a method of operating the operative field camera and the camera arm.
Figure 4B:
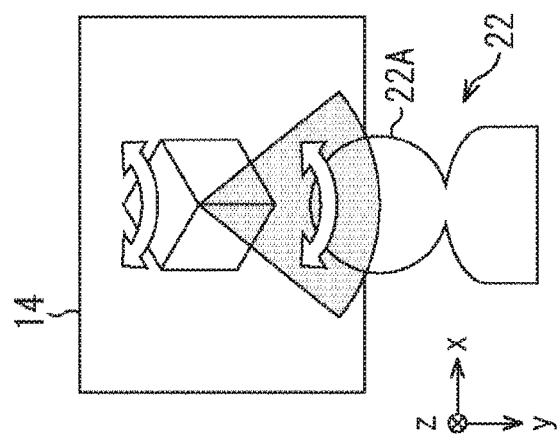
Figure 4A:
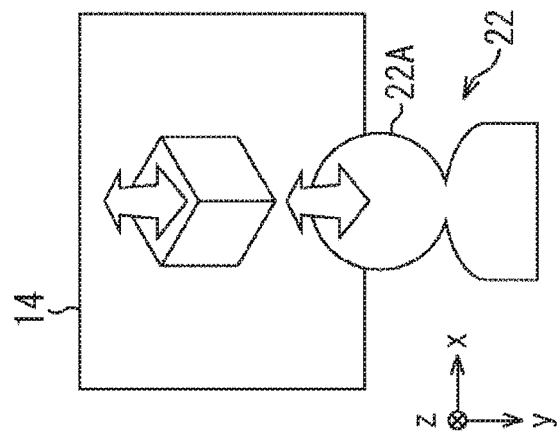

First, as illustrated in FIG. 4A, the zoom operation is performed by the operator 22 moving the head 22A in the z direction and moving close to or away from the display 14. The operative field image is scaled up by the head 22A moving close to the display 14, and the operative field image is scaled down by the head 22A moving away from the display 14. Note that the zoom operation may be performed by the operator 22 moving the head 22A in the y direction and making a nod-like motion.

Next, as illustrated in FIG. 4B, the pivot operation is performed by the operator 22 moving the head 22A in the x direction and making motions of, for example, tilting the head to a side or looking in the display 14 from a side. The imaging angle of the operative field image moves rightward by the head 22A moving rightward, and the imaging angle of the operative field image moves leftward by the head 22A moving leftward.

Besides, as illustrated in FIG. 4C, the move operation is performed by the operator 22 gazing at one point on the display 14. The position of the line of sight of the operator 22 on the operative field image displayed on the display 14 moves to the center of the screen.

Note that the operation (motion of the operator 22) for controlling the operation of each pattern (zoom, pivot, and move) of the operative field camera 11 and the camera arm 12 is not limited to that described with reference to FIGS. 4A, 4B, and 4C, and it is sufficient if the operation intuitively corresponds to the operation of each pattern of the operative field camera 11 and the camera arm 12.

Here, it is assumed that the operation for controlling operations of the respective zoom, pivot, and move patterns is accepted only while a single operation performed on the foot switch 18 is detected.

In other words, as illustrated in FIG. 5, operation for controlling operations of the respective zoom, pivot, and move patterns is accepted while the foot switch 18 is turned on by, for example, the pedal of the foot switch 18 being stepped by the leg 22B of the operator 22 or the like, and the operation control corresponding to the operation is performed in parallel. On the other hand, when the foot switch 18 is turned off by the leg 22B of the operator 22 being removed from the pedal of the foot switch 18, for example, operation for controlling operations of the respective zoom, pivot, and move patterns is not accepted, and no operation control is performed.

Figure 6B:
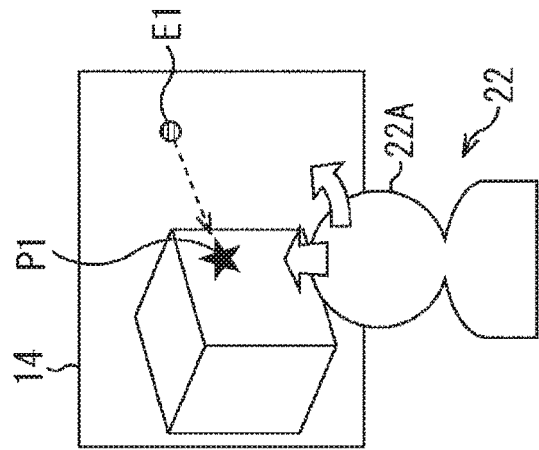
FIGS. 6A and 6B are diagrams illustrating exemplary operation control performed in parallel.
Figure 6A:
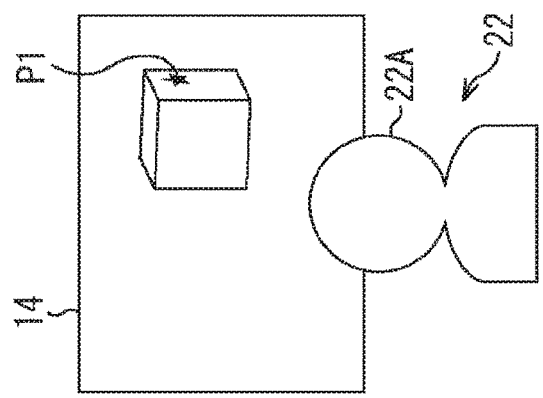

Here, as illustrated in FIG. 6A, it is assumed a case where the operator 22 attempts to clearly catch a point P1 reflected in the operative field image in the visual field.

In this case, while the pedal of the foot switch 18 is being stepped, the operator 22 sets a point of view at a position E1 corresponding to the point P1 on the display 14 and moves the head 22A close to the display while moving it rightward as illustrated in FIG. 6B, whereby the operation control of the respective move, pivot, and zoom patterns is performed in parallel.

In this manner, the operator 22 makes motions to intuitively correspond to operations of the respective patterns of the operative field camera 11 and the camera arm 12 using a single operation performed on the foot switch 18 as a trigger, whereby an optional point reflected in the operative field image can be clearly caught in the visual field.

<4. Exemplary Functional Configuration of Control Device>

Figure 7:
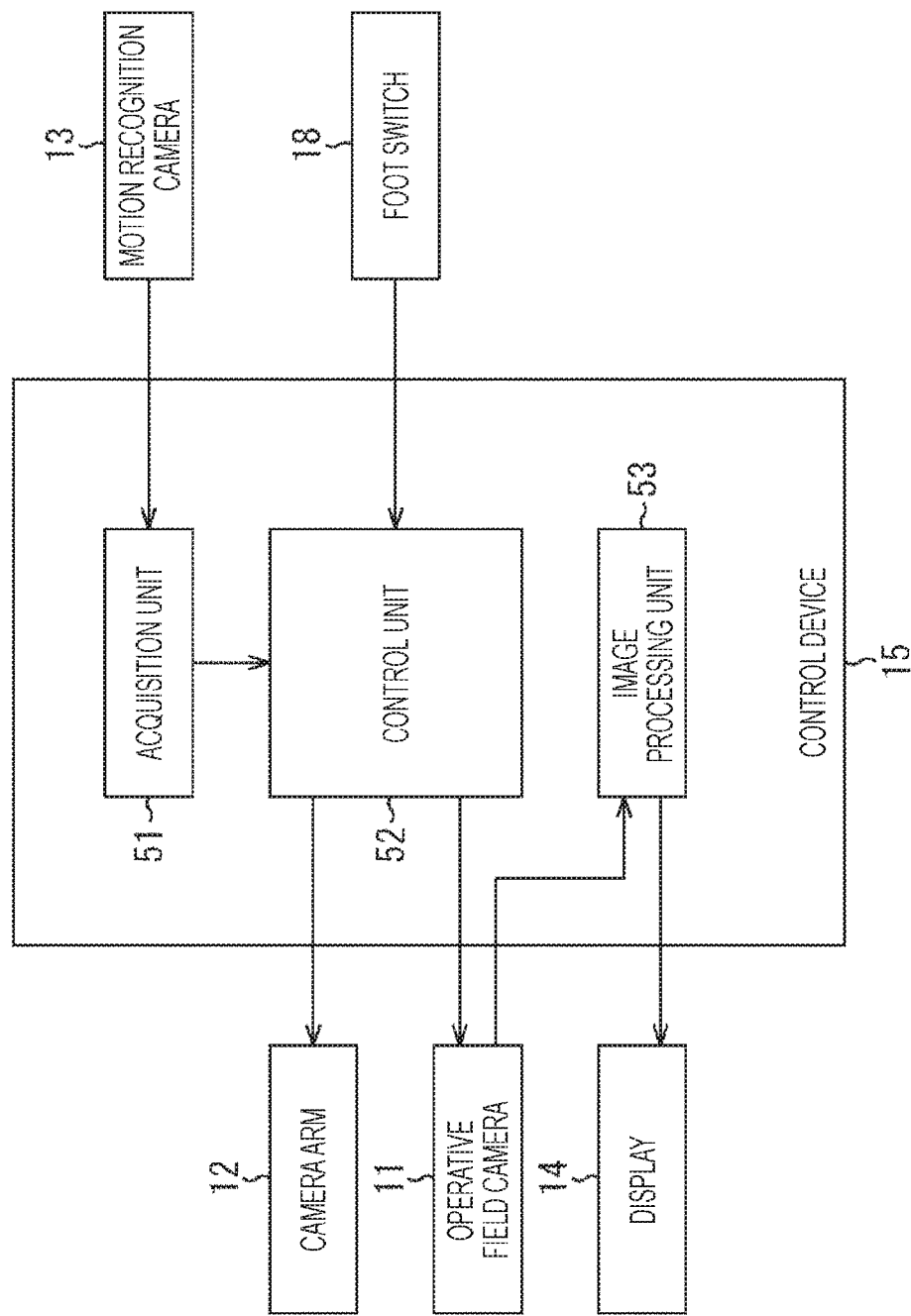
FIG. 7 is a block diagram illustrating an exemplary functional configuration of a control device.

FIG. 7 is a block diagram illustrating an exemplary functional configuration of the control device 15 in FIG. 2.

The control device 15 illustrated in FIG. 7 includes an acquisition unit 51, a control unit 52, and an image processing unit 53.

The acquisition unit 51 recognizes a motion (motion of the head 22A and position of a line of sight of the operator 22 on the screen of the display 14) of the operator 22 on the basis of the operator image transmitted from the motion recognition camera 13, thereby obtaining motion information indicating the motion. The obtained motion information is supplied to the control unit 52.

The control unit 52 controls a plurality of patterns of operations of the operative field camera 11 and the camera arm 12. In this example, the control unit 52 controls the operations of the respective zoom, pivot, and move patterns of the operative field camera 11 and the camera arm 12 as the operations of the plurality of patterns.

The control unit 52 controls a pattern corresponding to the motion information from the acquisition unit 51 using the operation information indicating a single operation performed on the foot switch 18, which is obtained from the foot switch 18, as a trigger.

For example, in a case where the motion information indicates operation (motion of the operator 22) corresponding to the zoom operation, the control unit 52 performs zoom control on the operative field camera 11 to perform the zoom operation while the operation information from the foot switch 18 is obtained.

Furthermore, in a case where the motion information indicates operation (motion of the operator 22) corresponding to the pivot operation, the control unit 52 performs drive control on the camera arm 12 to perform the pivot operation while the operation information from the foot switch 18 is obtained.

Moreover, in a case where the motion information indicates operation (motion of the operator 22) corresponding to the move operation, the control unit 52 performs drive control on the camera arm 12 to perform the move operation while the operation information from the foot switch 18 is obtained.

The image processing unit 53 applies, for example, various kinds of image processing for displaying an image to the operative field image captured by the operative field camera 11, and supplies the image to the display 14.

Note that the hardware configuration of the control device 15 can be achieved by an information processor including circuitry capable of implementing functions of the control device 15. The information processor included in the control device 15 includes, for example, a central processing unit (CPU), a read-only memory (ROM), a random access memory (RAM), a storage device, and an interface (I/F) for connecting to various external devices. The functions of the control device 15 is implemented by the CPU loading a program recorded in the ROM or the storage device beforehand in the RAM, executing the program, and connecting to various external devices via the I/F, for example.

Furthermore, the information processor may be configured by hardware, such as a field-programmable gate array (FPGA), and an application specific integrated circuit (ASIC). Moreover, a graphic processing unit (GPU) having a core number of 100 times or more than that of the CPU and is configured by a parallel architecture may be used as an information processor. It is possible to appropriately change the hardware configuration to be used depending on the technical level of the time of carrying out the present embodiment.

<5. Control Process Flow in Surgical System>

Figure 8:
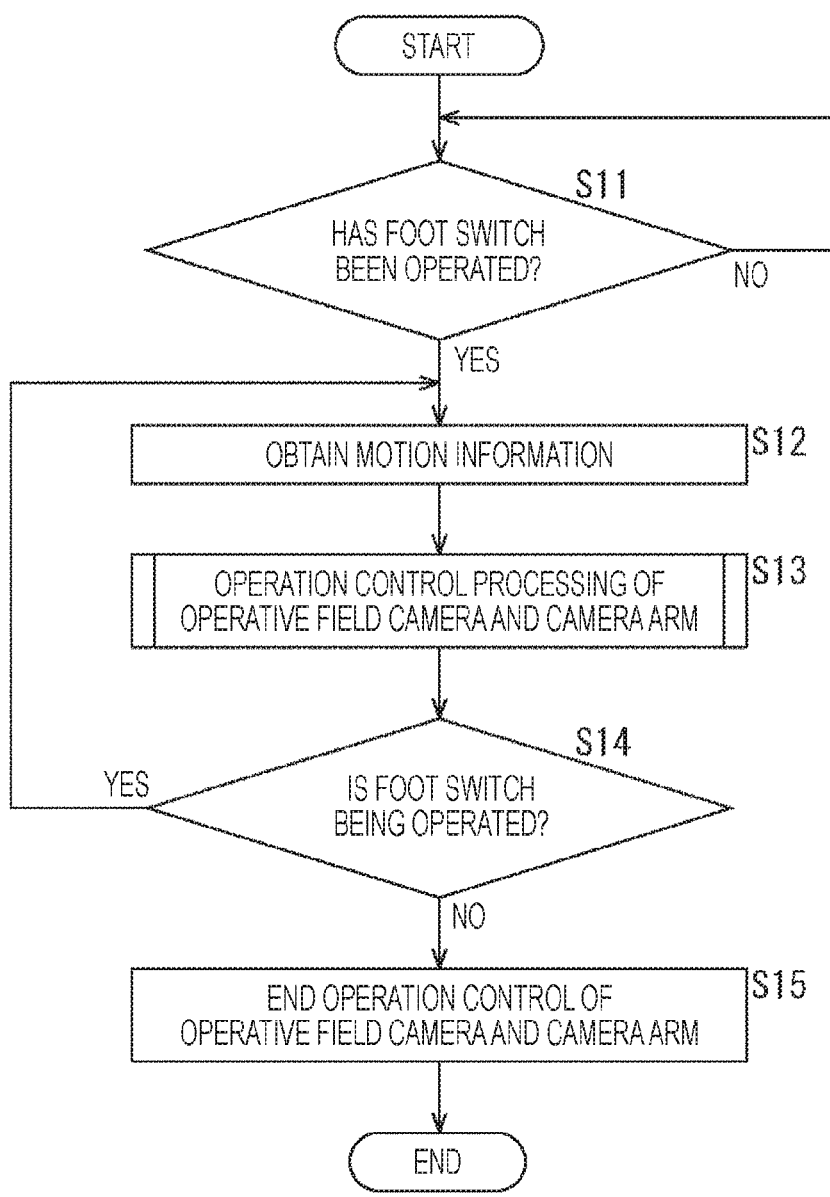
FIG. 8 is a flowchart illustrating a control process in the surgical system.

Next, a control process of the control device 15 in the surgical system 10 will be described with reference to a flowchart of FIG. 8.

In step S11, the control unit 52 determines whether or not the foot switch 18 has been operated on the basis of the presence or absence of the operation information from the foot switch 18.

The processing in step S11 is repeated until it is determined that the foot switch 18 has been operated. If it is determined that the foot switch 18 has been operated, the process proceeds to step S12.

In step S12, the acquisition unit 51 obtains motion information of the operator 22 on the basis of the operator image from the motion recognition camera 13.

In step S13, the control unit 52 performs operation control processing on the operative field camera 11 and the camera arm 12 on the basis of the motion information obtained by the acquisition unit 51. Details of the operation control processing performed on the operative field camera 11 and the camera arm 12 will be described later.

In step S14, the control unit 52 determines whether or not the foot switch 18 is being operated on the basis of the presence or absence of the operation information from the foot switch 18.

While it is determined in step S14 that the foot switch 18 is being operated, the processing of steps S12 and S13 is repeated, and the operation control processing of the operative field camera 11 and the camera arm 12 based on the motion information is performed continuously.

On the other hand, in a case where it is determined in step S14 that the foot switch 18 is not being operated, the process proceeds to step S15, and the control unit 52 terminates the operation control performed on the operative field camera 11 and the camera arm 12.

Next, details of the operation control processing performed on the operative field camera 11 and the camera arm 12 in step S13 in FIG. 8 will be described with reference to a flowchart of FIG. 9.

Figure 9:
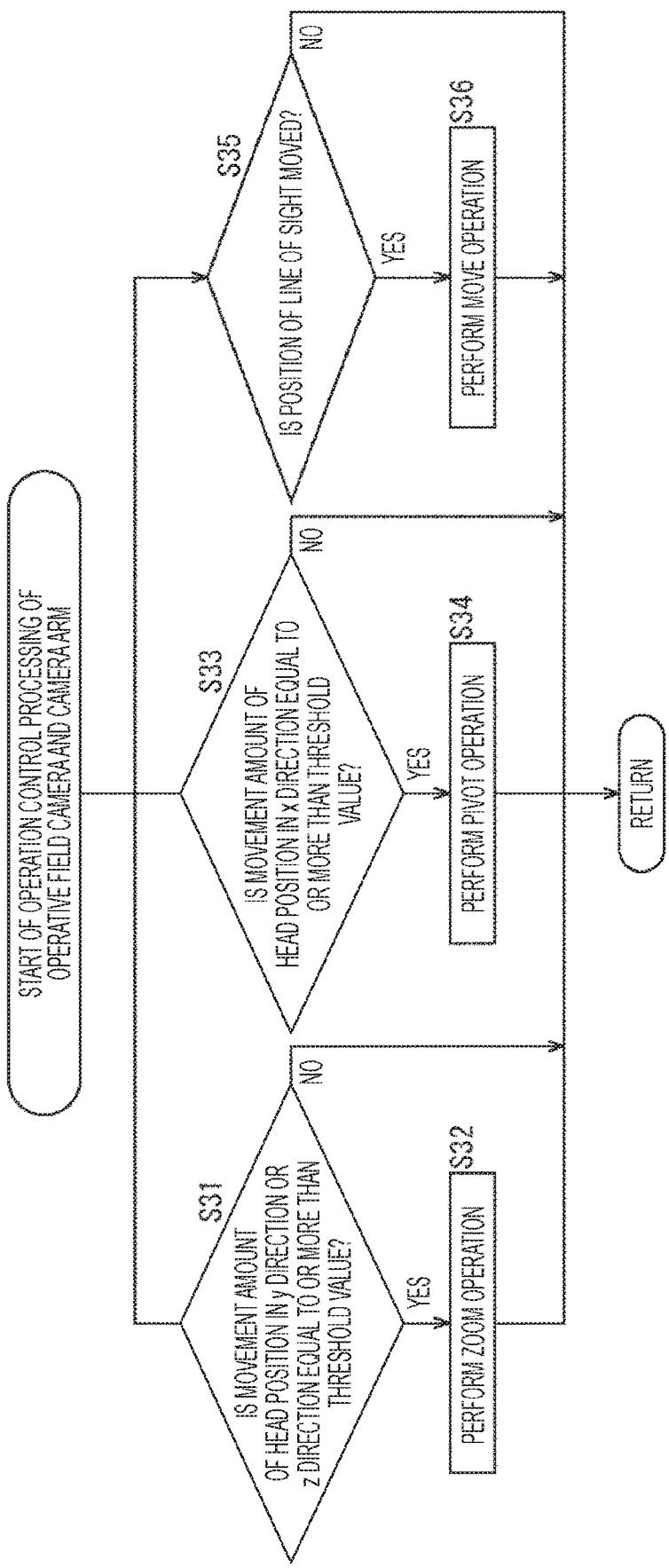
FIG. 9 is a flowchart illustrating details of an operation control process of the operative field camera and the camera arm.

Note that processing of steps S31 and S32, processing of steps S33 and S34, and processing of steps S35 and S36 are executed in parallel in the flowchart of FIG. 9.

In step S31, the control unit 52 determines whether or not an amount of movement of the position of the head 22A of the operator 22 in the y direction or in the z direction is equal to or more than a predetermined threshold value on the basis of the motion information obtained by the acquisition unit 51.

In a case where the amount of movement of the position of the head 22A in the y direction or in the z direction is determined to be equal to or more than the predetermined threshold value in step S31, the process proceeds to step S32, and the control unit 52 performs the zoom control on the operative field camera 11 such that the zoom operation corresponding to the moving direction of the position of the head 22A is performed.

On the other hand, in a case where the amount of movement of the position of the head 22A in the y direction or in the z direction is not equal to or more than the predetermined threshold value in step S31, step S32 is skipped. In other words, the zoom operation is not performed in this case.

Furthermore, in step S33, the control unit 52 determines whether or not an amount of movement of the position of the head 22A of the operator 22 in the x direction is equal to or more than a predetermined threshold value on the basis of the motion information obtained by the acquisition unit 51.

In a case where the amount of movement of the position of the head 22A in the x direction is determined to be equal to or more than the predetermined threshold value in step S33, the process proceeds to step S34, and the control unit 52 performs the drive control on the camera arm 12 such that the pivot operation corresponding to the moving direction of the position of the head 22A is performed.

On the other hand, in a case where the amount of movement of the position of the head 22A in the x direction is determined not to be equal to or more than the predetermined threshold value in step S33, step S34 is skipped. In other words, the pivot operation is not performed in this case.

Moreover, in step S35, the control unit 52 determines whether or not the position of the line of sight of the operator 22 is moved on the basis of the motion information obtained by the acquisition unit 51.

In a case where it is determined that the position of the line of sight is moved in step S35, the process proceeds to step S36, and the control unit 52 performs the drive control on the camera arm 12 such that the move operation corresponding to the movement of the position of the line of sight is performed.

On the other hand, in a case where it is determined that there is no movement of the position of the line of sight in step S35, step S36 is skipped. In other words, the move operation is not performed in this case.

As described above, the operation control of the respective zoom, pivot, and move patterns of the operative field camera 11 and the camera arm 12 are performed in parallel on the basis of the motion information.

According to the process described above, using a single operation performed on the foot switch 18 as a trigger, the operation control of the respective patterns of the operative field camera 11 and the camera arm 12 is performed on the basis of motions of the operator 22 intuitively corresponding to the operations of the respective patterns of the operative field camera 11 and the camera arm 12. Therefore, it becomes possible to implement operation without a burden on the operator and without complex operations, such as individually operating buttons and switches for operation control of respective patterns of the operative field camera 11 and the camera arm 12, for example.

Furthermore, it is not necessary to perform switch operation, such as switching the operation of each pattern of the operative field camera 11 and the camera arm 12, whereby an extra time for the operation can be reduced. Moreover, even in a case where an operation error occurs, the operation of the operative field camera 11 and the camera arm 12 can be immediately stopped by natural motions of the operator intuitively correcting the error or by the leg being removed from the foot switch 18.

<6. Variation>

Hereinafter, variations of the embodiment described above will be described.

(Another Exemplary Trigger)

Although a single operation performed on the foot switch 18 is used as a trigger for the operation control of the operative field camera 11 and the camera arm 12 in the embodiment described above, another operation may be used as the trigger. For example, input to a switch, a button, a kind of sensor, or the like not operated by the foot of the operator 22, or a result of voice recognition may be used as the trigger.

(Another Exemplary Move Operation)

In the embodiment described above, in the move operation, the follow-up operation of the camera arm 12 is performed on the basis of the position of the line of sight of the operator 22 with respect to the operative field image such that the position of the line of sight becomes the center of the screen. Accordingly, particularly in a case where the move operation is performed in parallel with the pivot operation or the zoom operation, the operator 22 can catch a desired range in the visual field without being conscious of the operation for the move operation.

However, in the move operation, the follow-up operation of the camera arm 12 can also be performed such that a characteristic point (e.g., tip of a surgical instrument, etc.) in the operative field image becomes the center of the screen.

(Another Exemplary Zoom Operation)

Although the zoom operation is performed on the basis of the optical zoom and digital zoom functions of the operative field camera 11 in the embodiment described above, the driving of the camera arm 12 may be controlled such that the operative field camera 11 itself moves close to or away from a subject to perform the zoom operation.

(Others)

In the embodiment described above, the operations of the operative field camera 11 and the camera arm 12 may not be limited to the operations of the respective zoom, pivot, and move patterns described above, and operation of any pattern may be performed.

Furthermore, in the descriptions above, objects to be controlled by the control unit 52 are the operative field camera 11 and the camera arm 12, and the operations of the plurality of patterns (zoom, pivot, and zoom) thereof are controlled in parallel. However, according to the technology according to the present disclosure, it is also possible to set any surgical instrument in the surgical system as an object to be controlled by the control unit 52, and to control a plurality of patterns of operations of the surgical instrument in parallel. In that case, it is sufficient if the surgical instrument is controlled on the basis of input not manually made by the operator, for example, and an auxiliary tool for surgery or a diagnosis is included in addition to the surgical instrument.

Moreover, although an exemplary case where the technology according to the present disclosure is applied to the surgical system using the operative field camera has been described above, a system to which the technology according to the present disclosure can be applied is not limited to the exemplary case. For example, the technology according to the present disclosure may be applied to an endoscope system or a microsurgery system.

Furthermore, an embodiment of the present technology is not limited to the embodiment described above, and various modifications are possible without departing from the gist of the present technology.

Moreover, the present technology can employ the following configurations.

(1)

A control device including:

a control unit that controls a plurality of patterns of operations of a surgical instrument; and an acquisition unit that obtains motion information indicating a motion of a user, in which the control unit controls the operations of the respective patterns corresponding to the motion information obtained by the acquisition unit in parallel using only a single operation performed by the user as a trigger.

(2)

The control device according to (1) described above, in which the control unit controls the operations of the respective patterns corresponding to the motion information in parallel only while the single operation is detected.

(3)

The control device according to (2) described above, in which the surgical instrument includes at least a camera and a camera arm supporting the camera, and the control unit performs control of a plurality of patterns of operations based on zoom control of the camera and drive control of the camera arm.

(4)

The control device according to (3) described above, in which the control unit controls the operations of the respective patterns corresponding to the motion information in parallel using only the single operation performed on a foot switch as a trigger.

(5)

The control device according to (3) or (4) described above, in which the motion information includes information indicating a motion of a head of the user.

(6)

The control device according to any one of (3) to (5) described above, in which the motion information includes information indicating a position of a line of sight of the user.

(7)

The control device according to (6) described above, in which the position of the line of sight of the user includes a position of the line of sight detected with respect to a display on which an image captured by the camera is displayed.

(8)

A control method performed by a control device that controls a plurality of patterns of operations of a surgical instrument, the method including steps of:

obtaining motion information indicating a motion of a user; and controlling the operations of the respective patterns corresponding to the obtained motion information in parallel using only a single operation performed by the user as a trigger.

(9)

A surgical system including:

a surgical instrument; and a control device that controls the surgical instrument, in which the control device includes:

a control unit that controls a plurality of patterns of operations of the surgical instrument; and an acquisition unit that obtains motion information indicating a motion of a user, and the control unit controls the operations of the respective patterns corresponding to the motion information obtained by the acquisition unit in parallel using only a single operation performed by the user as a trigger.

REFERENCE SIGNS LIST

10 Surgical system
11 Operative field camera
12 Camera arm
13 Motion recognition camera
14 Display
15 Control device
17 Microphone
18 Foot switch
51 Acquisition unit
52 Control unit
53 Image processing unit

The invention claimed is:

1. A control device, comprising:
circuitry configured to:
obtain motion information indicating a motion of a user, wherein the motion of the user includes a motion of a head of the user;
determine that the motion of the head of the user is in one of a first direction or a second direction, based on the obtained motion information, wherein the first direction is perpendicular to the second direction; and
execute an operation of at least one pattern of a plurality of patterns of a surgical instrument based on the determined motion of the head of the user, wherein
an operation of a first pattern of the plurality of patterns of the surgical instrument is executed, in a case where the determined motion of the head of the user is in the first direction,
an operation of a second pattern of the plurality of patterns of the surgical instrument is executed, in a case where the determined motion of the head of the user is in the second direction,
in each of the operation of the first pattern and the operation of the second pattern, an imaging centre of the surgical instrument is fixed, the operation of the first pattern is different from the operation of the second pattern, and the operation of the at least one pattern of the plurality of patterns of the surgical instrument is executed in parallel with reception of information indicating a single operation by the user as a trigger.

2. The control device according to claim 1, wherein the circuitry is further configured to execute the operation of the at least one pattern only when the single operation is detected.

3. The control device according to claim 2, wherein
the surgical instrument includes at least one of a camera or a camera arm supporting the camera, and
the circuitry is further configured to execute the operation of the at least one pattern of the plurality of patterns based on a zoom control of the camera and a drive control of the camera arm.

4. The control device according to claim 3, wherein the single operation is performed based on a foot switch as the trigger.

5. The control device according to claim 3, wherein the motion information further includes information indicating a position of a line of sight of the user.

6. The control device according to claim 5, wherein the position of the line of sight of the user is indicated with respect to a display on which an image captured by the camera is displayed.

7. A control method comprising:
obtaining motion information indicating a motion of a user, wherein the motion of the user includes a motion of a head of the user;
determine that the motion of the head of the user is in one of a first direction or a second direction, based on the obtained motion information, wherein the first direction is perpendicular to the second direction; and
executing an operation of at least one pattern of a plurality of patterns of a surgical instrument based on the determined motion of the head of the user, wherein
an operation of a first pattern of the plurality of patterns of the surgical instrument is executed, in a case where the determined motion of the head of the user is in the first direction,
an operation of a second pattern of the plurality of patterns of the surgical instrument is executed, in a case where the determined motion of the head of the user is in the second direction, in each of the operation of the first pattern and the operation of the second pattern, an imaging centre of the surgical instrument is fixed,
the operation of the first pattern is different from the operation of the second pattern, and
the operation of the at least one pattern of the plurality of patterns of the surgical instrument is executed in parallel with reception of information indicating a single operation by the user as a trigger.

8. A surgical system, comprising:
a surgical instrument; and
a control device configured to control the surgical instrument, wherein the control device includes circuitry configured to:
obtain motion information indicating a motion of a user, wherein the motion of the user includes a motion of a head of the user;
determine that the motion of the head of the user is in one of a first direction or a second direction, based on the obtained motion information, wherein the first direction is perpendicular to the second direction; and
execute an operation of at least one pattern of a plurality of patterns of the surgical instrument based on the determined motion of the head of the user, wherein
an operation of a first pattern of the plurality of patterns of the surgical instrument is executed, in a case where the determined motion of the head of the user is in the first direction,
an operation of a second pattern of the plurality of patterns of the surgical instrument is executed, in a case where the determined motion of the head of the user is in the second direction,
in each of the operation of the first pattern and the operation of the second pattern, an imaging centre of the surgical instrument is fixed,
the operation of the first pattern is different from the operation of the second pattern, and
the operation of the at least one pattern of the plurality of patterns of the surgical instrument is executed in parallel with reception of information indicating a single operation by the user as a trigger.

* * * * *